United States Patent

Cody et al.

[11] Patent Number: 5,807,568
[45] Date of Patent: Sep. 15, 1998

[54] ENHANCED DELIVERY OF TOPICAL COMPOSITIONS CONTAINING FLURBIPROFEN

[75] Inventors: Sharon L. Cody, Philadelphia; Richard D. Fegley; Michael R. Hoy, both of Sellersville, all of Pa.

[73] Assignee: McNeil-PPC, Inc., Skillman, N.J.

[21] Appl. No.: 744,901

[22] Filed: Nov. 8, 1996

Related U.S. Application Data

[63] Continuation of Ser. No. 364,882, Dec. 27, 1994, abandoned.

[51] Int. Cl.$^6$ ................................................. A61K 9/14
[52] U.S. Cl. ........................... 424/444; 424/484; 424/488
[58] Field of Search ................................... 424/444, 484, 424/488; 4241/444, 484, 488

[56] References Cited

U.S. PATENT DOCUMENTS

| | | | |
|---|---|---|---|
| 4,185,100 | 1/1980 | Rovee et al. | 424/240 |
| 4,393,076 | 7/1983 | Noda et al. | 424/317 |
| 4,472,376 | 9/1984 | Kamishita | 424/81 |
| 4,533,546 | 8/1985 | Kishi et al. | 424/81 |
| 4,545,992 | 10/1985 | Kamishita | 514/161 |
| 4,555,524 | 11/1985 | Gruber et al. | 514/570 |
| 4,557,934 | 12/1985 | Cooper | 424/128 |
| 4,559,326 | 12/1985 | Crawford et al. | 514/23 |
| 4,572,832 | 2/1986 | Kigasawa et al. | 424/19 |
| 4,628,053 | 12/1986 | Fries | 514/222 |
| 4,678,666 | 7/1987 | Nozawa et al. | 424/81 |
| 4,695,465 | 9/1987 | Kigasawa et al. | 424/449 |
| 4,704,406 | 11/1987 | Stanislaus et al. | 514/570 |
| 4,824,841 | 4/1989 | Chiesi et al. | 514/226.5 |
| 4,851,444 | 7/1989 | Sunshine et al. | 514/570 |
| 4,942,167 | 7/1990 | Chiesi et al. | 514/226.5 |
| 4,954,487 | 9/1990 | Cooper et al. | 514/159 |
| 5,025,004 | 6/1991 | Wu et al. | 514/165 |
| 5,093,133 | 3/1992 | Wisniewski et al. | 424/484 |
| 5,104,656 | 4/1992 | Seth et al. | 424/401 |
| 5,145,663 | 9/1992 | Simmons | 424/47 |

FOREIGN PATENT DOCUMENTS

| | | |
|---|---|---|
| Sho 56-154413 | 11/1981 | Japan . |
| Sho 63-119420 | 5/1988 | Japan . |
| Hei 4-99719 | 3/1992 | Japan . |
| 93/17710 | 9/1993 | WIPO . |

*Primary Examiner*—James H. Reamer
*Attorney, Agent, or Firm*—Bernard F. Plantz

[57] ABSTRACT

The present invention is directed to flurbiprofen-containing compositions for topical administration comprising about 0.5 to 10% flurbiprofen; about 10 to 80% of a lower alcohol; about 0 to 25% of a glycol; about 0 to 5% of a gelling agent; an amount of a pH adjusting agent sufficient to adjust the pH of the composition to a range of from about 2 to less than 4.5; and water in an amount sufficient to make up the balance of the composition, and methods for delivering flurbiprofen-containing compositions through the skin.

22 Claims, 3 Drawing Sheets

5,807,568

ENHANCED DELIVERY OF TOPICAL COMPOSITIONS CONTAINING FLURBIPROFEN

This is a continuation of application Ser. No. 08/364,882, filed Dec. 27, 1994, now abandoned.

This invention relates to an improved method for the percutaneous delivery of the drug flurbiprofen in order to treat conditions in the joints or soft tissue beneath the skin (e.g., inflammation and/or pain). More particularly, this invention relates to flurbiprofen-containing pharmaceutical compositions which show improved skin penetrability of the flurbiprofen active ingredient.

BACKGROUND OF THE INVENTION

Flurbiprofen is a well-known, non-steroidal, anti-inflammatory drug (NSAID) having anti-inflammatory properties. It is generally used to relieve pain and to treat inflammation, especially in patients suffering from severe or chronic arthritis.

Flurbiprofen is mostly administered orally. One disadvantage of the oral administration of flurbiprofen-containing compositions is that the patient is likely to experience unpleasant side effects, including gastrointestinal irritation, and even liver and kidney problems. Accordingly, it is desirable to produce a flurbiprofen-containing composition which may be applied topically and yet is as safe and effective as the flurbiprofen-containing tablets or capsules which are orally consumed.

Flurbiprofen has been marketed as adhesive plasters in Japan, e.g., "ADOFEED", "ZEPOLAS", and "STAYBAN". ADOFEED, ZEPOLAS, STAYBAN are white to light yellow adhesive plasters containing isopropyl myristate and polysorbate 80. ADOFEED and ZEPOLAS plasters have a pH of 5 to 7.

Japanese Kokai Patent Application No. 56[1981]-154413, filed in the name of Mori et al., discloses a topical anti-inflammatory analgesic containing flurbiprofen.

Kokai Patent Application 56[1981]-154413 states that flurbiprofen is solubilized in a terpene or higher fatty acid ester, then mixed with surfactants and water to form an oil-in-water emulsion. The oil-in-water emulsion is mixed with an aqueous base made of cellulose derivatives, polyacrylate alkali metal salts, gelatin, multivalent alcohols, and water, and the pH is adjusted to 5 to 8. The compositions so obtained are spread on a base cloth and utilized as a transdermal patch.

U.S. Pat. No. 4,393,076, issued in the name of Noda et al., describes an anti-inflammatory analgesic gel composition comprising (1) ketoprofen and/or flurbiprofen, (2) a glycol, a lower alcohol, water or a lower alcohol-water mixture, (3) a gel-forming agent and, optionally, (4) a solubilizing agent and/or a non-ionic surface-active agent and (5) a neutralizing agent. It is stated that preferably the gel composition should be kept at a nearly neutral pH in the range between 4.5 to 7, and more preferably at a pH of 5.0 to 6.5.

U.S. Pat. No. 4,472,376, issued in the name of Kamishita, broadly describes a flurbiprofen-containing gel composition which is intended to be inserted into the rectum, vagina or urethra, and which comprises a mixture of an aqueous solution of carboxyvinyl polymer with a water-soluble basic compound and a pharmaceutical ingredient, wherein the mixture is a gel having a pH of from 4 to 10 and a viscosity of from 5,000 to 100,000 centipoises at 20° C.

U.S. Pat. No. 4,533,546, issued in the name of Kishi, discloses flurbiprofen containing hydroalcoholic gels having a pH in the range of from 7.0 to 9.0. The gel ointment comprises a phenylacetic acid anti-inflammatory compound, a carboxyvinyl polymer, a water-soluble organic amine, e.g., triethanolamine, a lower alcohol and water, wherein the amount of organic amine is such that the gel ointment has a pH in the range of 7.0 to 9.0, preferably 7.0 to 8.0, and more preferably 7.3 to 7.8.

U.S. Pat. No. 4,545,992, issued in the name of Kamishita, describes a pharmaceutical preparation for external use which comprises flurbiprofen which is dissolved in an adjuvant selected from the group consisting of peppermint oil, methyl salicylate, ethyl salicylate and monoglycol salicylate, and a base such as sodium hydroxide.

Japanese Kokai Patent Application No. 63[1988]-119420, filed in the name of Nakagawa et al., discloses a foam aerosol anti-inflammatory analgesic preparation made of an anti-inflammatory analgesic such as flurbiprofen, a surfactant, water, a powder, a propellant, and optionally a lower alcohol and other dissolution aids including propylene glycol.

Japanese Kokai Patent Application No. 4[1992]-99719, filed in the name of Mori, discloses an external pasting agent for use as a transdermal patch wherein the paste is comprised of at least one component selected from fatty acids and their derivatives, animal and plant oils and fats, polyvalent alcohols including propylene glycol and polyethylene glycol, and water. In Test Example 2, the pH of the flurbiprofen containing composition of Application Example 1 was varied from 5.14 to 8.88, the permeation rate of the drugs was measured, and it was observed that the permeation rate of drug increased as the pH of the composition approached 5.

World Patent No. 93/17710, issued in the name of Konno et al., describes the use of triethylene glycol in conjunction with terpenes to enhance percutaneous absorption of non-steroidal anti-inflammatory agents such as flurbiprofen.

U.S. Pat. No. 4,185,100, issued in the name of Rovee et al., describes a method of topical treatment of an inflammatory skin condition by applying to the affected area a composition comprising a non-steroidal anti-inflammatory agent and an anti-inflammatory cortico-steroid, wherein the composition may be in the form of a cream, a gel, an ointment, a powder, an aerosol, or a solution.

U.S. Pat. No. 4,704,406, issued in the name of Stanislaus et al., discloses a spray pharmaceutical formulation containing a solvent mixture of at least one volatile solvent such as ethanol, propanol and isopropanol, at least one non-volatile solvent such as higher mono- and poly-functional alcohols, an arylalkanoic acid such as flurbiprofen, and optionally a film forming component such as polyacrylates.

The flurbiprofen containing compositions described above have at least one disadvantage in that the amount of drug delivered transdermally is not maximized. Accordingly, there exists a need for a percutaneous delivery system for the drug flurbiprofen which optimizes the delivery of flurbiprofen through the skin.

It is therefore an object of the present invention to provide a flurbiprofen-containing composition which is more effective for purposes of percutaneous delivery of flurbiprofen through the skin.

SUMMARY OF THE INVENTION

The present invention is directed to a pharmaceutical composition exhibiting an optimal flux or diffusion for the topical delivery of flurbiprofen. It has been discovered that the formulation of a composition at the proper pH was important to maximize the flux of flurbiprofen through the skin. In contrast to the prior art which broadly teaches flurbiprofen-containing topical and transdermal compositions having a pH in the range of about 4 to 10, and typically in the neutral range between about 4.5 to about 7, so as to avoid irritation to the skin, it has been surprisingly found that hydroalcoholic gel compositions having a pH of from about 2 to less than about 5.5 exhibit the highest flux or rate of drug delivery, and that the rate of drug delivery actually decreases when such compositions have a pH of about 5.5 or higher.

The pH range in which flux rates are maximized will shift depending upon the choice of ingredients, and the relative proportions thereof, and the pKa of the composition. It has further been found that, as a rule of thumb, in order to optimize rates of drug delivery, the optimal pH for hydroalcoholic gel compositions should be approximately one pH unit below the apparent pKa of the active ingredient in the topical composition. By "apparent pKa" is meant the pKa of the active ingredient in its present or given environment. For example, in a 30% (by weight of the total weight of the composition) isopropyl alcohol solution containing flurbiprofen and having an apparent pKa of 5.3, the optimal pH is preferably about 4.3.

As embodied and fully described herein the present invention provides a hydroalcoholic composition with a pH in the range of from about 2 to less than 4.5. In preferred embodiments of the invention, the flurbiprofen-containing composition comprises, by weight of the total weight of the composition, about 0.5 to 10% flurbiprofen; about 10 to 80% of a volatile alcohol, preferably a lower alcohol; about 0 to 25% of a non-volatile solvent, preferably a glycol; about 0 to 5% of a gelling agent; an amount of a pH adjusting agent sufficient to adjust the pH of the composition to a range of from about 2 to less than 4.5; and water in an amount sufficient to make up the balance of the composition. In more preferred embodiments of the invention the composition is a gel which comprises, about 1 to 5% flurbiprofen; about 30 to 55% of a lower alcohol; about 5 to 15% of a glycol; about 0.5 to 2% of a gelling agent; an amount of a pH adjusting agent sufficient to adjust the pH to a range of from about 2 to less than 4.5; and water q.s. to 100%.

In an especially preferred embodiment, the composition is a hydroalcoholic gel comprising, about 4% flurbiprofen; about 30% of a lower alcohol; about 10% of a glycol; about 2% of a gelling agent; about 0.05% of a pH adjusting agent sufficient to adjust the pH to a range to about 4; about 55% water, and optionally a penetration enhancer. In preferred embodiments, the compositions of the invention may consist essentially of the above-described components.

The invention further comprises methods for delivering flurbiprofen through the skin in order to treat conditions situated beneath or on the skin, which comprise the step of topically administering the flurbiprofen-containing-compositions herein described to the skin of the patient, which are either occluded or left unoccluded.

DETAILED DESCRIPTION OF THE INVENTION

Figure 1:
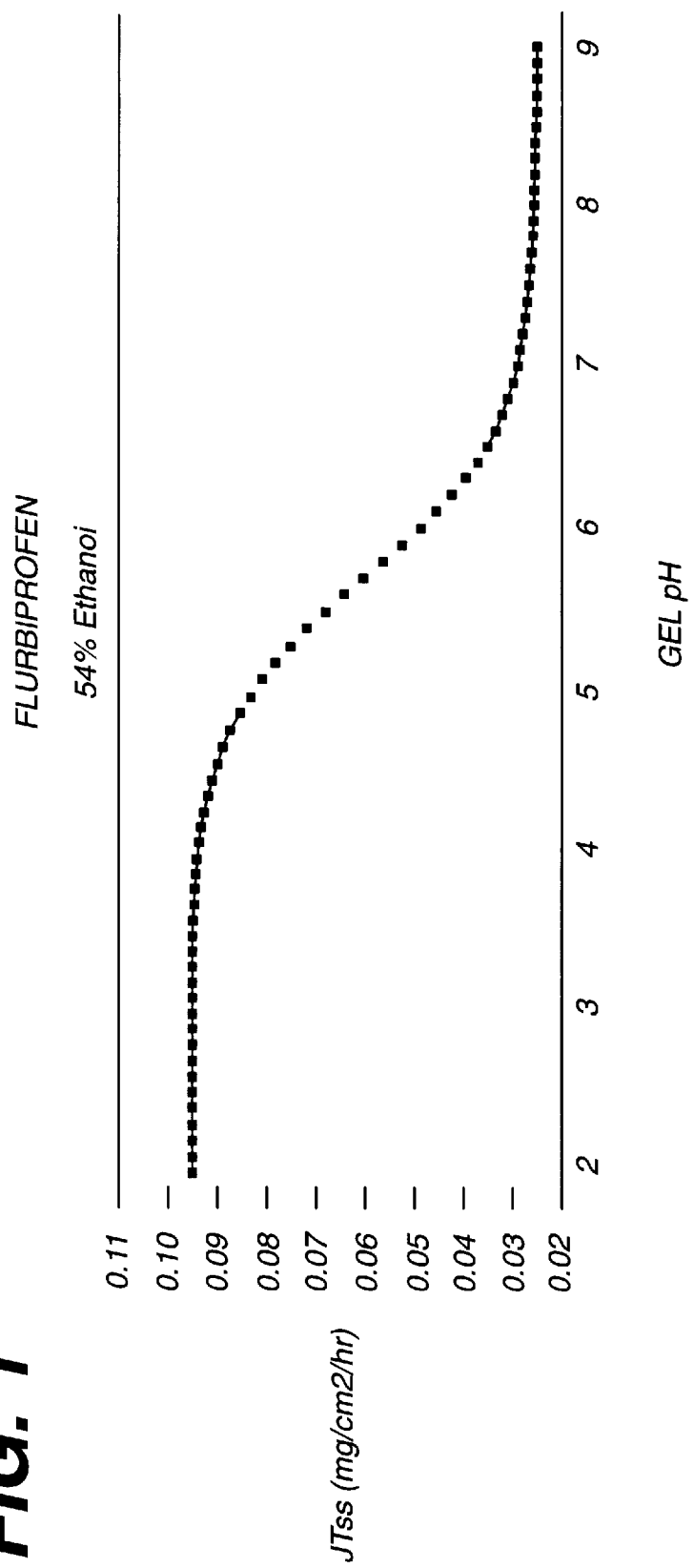
FIG. 1 is a graph which plots simulated data showing the theoretical effect of pH on the diffusion of flurbiprofen, in a gel containing 2% flurbiprofen, 54% ethanol and having a pKa of 5.7, as determined from Fick's Second Law.

By topical administration, as used herein, is meant directly laying or spreading upon epidermal tissue, specially outer skin or membrane.

As used herein all percentages are by weight of the total composition unless otherwise specified.

The following terms are used interchangeably herein:
"active", "drug", and "active ingredient" are interchangeable;
"diffusion" and "flux" are interchangeable;
"flux rate" and "rate of drug delivery" are interchangeable.

By the term "pH", as used herein, is meant "apparent pH" wherein the pH measurement is carried out on the flurbiprofen-containing composition in final form, for example, by measuring the pH of the gel, spray, ointment, or lotion.

Preferably, the flurbiprofen-containing compositions of the present invention are spreadable, semi-solid, jelly-like gels, which may be occluded (e.g., covered with a permeable, semi-permeable, or impermeable film or barrier) or remain unoccluded. However, the compositions of the invention may also take the form of a spray, an aerosol, a lotion, a cream, or an ointment. The terms "gel", "spray", "aerosol", "lotion", "cream", and "ointment", are used herein as defined in *Remington Pharmaceutical Sciences,* 17th Edition, 1985, and are incorporated herein by reference.

In a preferred embodiment of the invention, the compositions of the invention are hydroalcoholic gels made from flurbiprofen, a lower alcohol, a gelling agent and water. The flurbiprofen useful in accordance with this invention includes the pharmaceutically acceptable salts and esters of flurbiprofen, and further includes the conventionally used racemic mixture which comprises the S- and R- enantiomers of flurbiprofen and also includes substantially pure S-flurbiprofen and substantially pure R-flurbiprofen. Substantially pure S-flurbiprofen for the purposes of this specification means at least 90% by weight S-flurbiprofen and 10% or less by weight of the R-enantiomer of flurbiprofen. Substantially pure R-flurbiprofen for the purposes of this specification means at least 90% by weight R-flurbiprofen and 10% or less by weight of the S-enantiomer of flurbiprofen. The compositions of the invention contain from about 0.5 to 10% flurbiprofen (U.S. Pharm.), preferably from about 1.0 to 5.0%, more preferably from 2.0 to 4.0%, and most preferably about 4.0%.

The composition of the invention also contains about 10 to 80% of a volatile solvent, preferably a lower alcohol, and preferably in an amount between about 30 to 55%, and more preferably about 30%. Preferably the amount used will produce a saturated or almost saturated solution of flurbiprofen in the final preparation. The minimum amount of alcohol used is the amount necessary to dissolve the only very slightly soluble flurbiprofen. Thus, one would normally use more alcohol with a greater amount of flurbiprofen than with a lesser amount of flurbiprofen. Any pharmaceutically acceptable lower alcohol may be used, including for example propanol, ethanol, denatured ethanol, and isopropanol. Isopropanol and ethanol are preferred. Isopropanol is most preferred.

Solubilizing agents known to those skilled in the art, including for example those identified in U.S. Pat. No. 4,393,076, as well as dimethyl isosorbide, N-methyl-2-pyrrolidone, and the like, further may be included. Solubilizing agents may be added in amounts necessary to solubilize the flurbiprofen, such as, for example, from about 0 to 20% by weight, preferably from about 0 to 15%, most preferably from about 0 to 10%.

Optionally, the compositions of the invention may comprise a non-volatile solvent, such as glycol, to improve the spreading properties and aesthetics of the composition, and to minimize any balling up or drying of the composition when it is rubbed on the skin. Preferably the composition comprises up to about 50% of at least one glycol, more preferably from about 5 to 30%, even more preferably from about 5 to 15%, and most preferably about 10%. The term glycol, as used herein, includes butylene glycol, propylene glycol, polypropylene glycol, polyethylene glycol, polyethylene glycol dodecyl ether, glycerine, and a mixture of at least two or more of these glycols. Propylene glycol and/or polyethylene glycol are preferred.

When used in gel form, the compositions of the invention comprise a gelling agent in the amount of up to about 5%, preferably from about 0.5 to 2%, and more preferably about 2%. Examples of suitable gelling agents include carboxyvinyl polymers, hydroxycellulose, hydroxyethyl cellulose ("HEC"), methylcellulose, hydroxypropylmethyl cellulose ("HPMC"), carboxymethyl cellulose, hydroxypropyl cellulose ("HPC"), alginic acid-propylene glycol ester, or polyacrylic acid polymer ("PAA"). Preferred gelling agents are HPC, available from Hercules, Inc. as KLUCEL HF, and PAA, available from B. F. Goodrich Chemical Co. as CARBOPOL, CARBOMER 934 NF, or CARBOMER 980 NF. Other gelling agents may be alternatively used in this invention provided they are compatible with the hydroalcoholic system, i.e., capable of forming a gel with the amount of alcohol and water required to solubilize flurbiprofen. Many well known gelling agents may not, however, form gels under these conditions in this system.

Preferably, the hydroalcoholic gels for use in the process of the present invention will have a viscosity of within the range of about 50,000 to 1.5 million centipoises (cps), preferably between about 300,000 to 1.0 million cps, and even more preferably between about 350,000 to 800,000 cps, when measured using a Brookfield type LV series viscometer with helipath stand at ambient temperature (i.e., 20°–25° C.) and with a 0.5 inch helipath and T-spindle (size "E") rotating at 0.3 RPM in a sample size ranging from 15 to 20 grams. However, even a broader range of viscosity is possible.

As indicated above and in FIG. 1, the rate of delivery of flurbiprofen percutaneously has surprisingly been found to be maximized at pH levels of from about 2 to about 5.5, preferably from about 2 to less than 4.7, more preferably from about 2.5 to less than 4.5, even more preferably from about 3.5 to 4, and most preferably at about 4.0. Flurbiprofen and also some gelling agents useable in accordance with the present invention are generally acidic and thus bring the pH at or below the desirable range. Alternatively, the pH of the composition may be adjusted to the desirable range by the addition of a pH adjusting agent, such as, for example, diisopropanolamine, diisopropylamine, triethanolamine, diethylamine, triethylamine, sodium hydroxide, potassium hydroxide or any other compatible, pharmaceutically acceptable base or alkalizing agent. These neutralizing agents may preferably be used in an amount by weight of up to about 1%, preferably less than about 0.5%, more preferably less than 0.1%, even more preferably about 0.05%, and most preferably less than about 0.05% by weight.

The compositions of the invention may further comprise from about 0 to 10%, preferably from about 0 to 5%, even more preferably from about 0.1 to 2%, penetration enhancing compositions which provide improved transepidermal or percutaneous delivery of flurbiprofen, when compared to other compositions which lack the presence of such penetration enhancing compositions. Such compositions are well known in the art and are described in, for example, World Patent No. 93/17710, the disclosure of which is hereby incorporated by reference. Suitable penetration enhancers include terpenes, terpene alcohols and essential oils. Examples of such penetration enhancers are d-limonene, terpinen-4-ol, menthone, 1,8-cineole, 1-pinene, a-terpineol, carveol, carvone, pulegone, piperitone, ascaridole, ylang ylang, anise, chenopodium, eucalyptus, 3-carene, cyclohexene oxide, limonene oxide, a-pinene oxide, cyclopentene oxide, 7-oxabicyclo[2.2.1]-heptane, eucalyptol, peppermint oil and the like. Preferred penetration enhancing compositions are d-limonene in an amount of about 0.5%.

Preservatives such as methylparaben and propylparaben and other pharmaceutically acceptable preservatives may be added to the gels to inhibit microbial activity, in amounts from about 0 to 2%, with about 1% being preferred.

Emollients, humectants, counterirritants, dyes, talcs, and other pharmaceutical excipients as well as fragrances may be added to the basic formulations of the invention, in amounts of from about 0 to 5.0%, with about 0 to 2.0% being preferred, and about 1.0% more preferred.

The effectiveness of the invention is demonstrated by the following examples. The examples are not intended to be limiting of the scope of the invention but read in conjunction with the detailed and general description above, provide further understanding of the present invention and an outline of the process for preparing the compositions of the invention.

EXAMPLES

COMPARATIVE EXAMPLE 1

The following formulation was used in Example 1 and was made into a gel by the procedure which follows:

| Component | Amount grams |
| --- | --- |
| Flurbiprofen | 2.0 |
| Ethanol USP | 54.0 |
| Propylene Glycol | 5.0 |
| Klucel HF | 2.5 |
| pH Adjusting Agent (conc. NaOH) | 0.49 |
| Purified Water | 36.01 |

The gel had a pH of 6.5.

Manufacturing Directions:

1) Weigh lower alcohol (e.g., ethanol).

2) Add flurbiprofen to alcohol and mix until flurbiprofen is dissolved.

3) Add glycol to the solution and mix.

4) Add about 20 grams of water and continue mixing.

5) Add pH adjusting agent (e.g., conc. NaOH) to the solution as appropriate and mix.

6) Add q.s. water and mix.

7) Add Klucel while mixing and continue mixing until Klucel is dissolved.

EXAMPLES 2 TO 4

Following the procedure described in Example 1, but using the following formulations shown as the ingredients thereof, in each case a hydroalcoholic gel was obtained, having a pH indicated.

EXAMPLE 2

| Component | Amount grams |
| --- | --- |
| Flurbiprofen | 2.0 |
| Ethanol USP | 54.0 |
| Propylene Glycol | 5.0 |
| Klucel HF | 2.5 |
| Purified Water | 36.5 |

The gel composition had a pH of 3.9.

EXAMPLE 3

| Component | Amount grams |
| --- | --- |
| Flurbiprofen | 2.0 |
| Ethanol USP | 54.0 |
| Propylene Glycol | 5.0 |
| Klucel HF | 2.5 |
| Triethanolamine | 0.1 |
| Purified Water | 36.4 |

The gel had a pH of 5.0.

EXAMPLE 4

| Component | Amount Grams |
| --- | --- |
| Flurbiprofen | 2.0 |
| Ethanol USP | 54.0 |
| Propylene Glycol | 5.0 |
| Klucel HF | 2.5 |
| pH Adjusting Agent (1N HCl) | 1.2 |
| Purified Water | 35.3 |

The gel had a pH of 2.2.

EXAMPLES 5 TO 13

For Examples 5 to 13, using the following procedure described below, and using the following formulations shown as the ingredients thereof, in each case a hydroalcoholic gel was obtained, having a pH as indicated.

Manufacturing Directions:

1) Weigh lower alcohol.

2) Add flurbiprofen to the lower alcohol and mix until flurbiprofen is dissolved.

3) Add glycols and terpenes to the flurbiprofen/alcohol solution as appropriate and mix.

4) Add water and continue mixing.

5) Add carbomer while mixing and continue mixing until carbomer is dissolved.

6) Add pH adjusting agent and continue mixing until the gel is substantially uniform.

EXAMPLE 5

| Component | Amount grams |
| --- | --- |
| Flurbiprofen | 5.0 |
| Isopropyl Alcohol | 30.0 |
| Propylene Glycol | 5.0 |
| Polyethylene Glycol 400 | 5.0 |
| Carbomer 980 NF | 2.0 |
| Diisopropanolamine | <0.1 |
| Purified Water | q.s.a.d. |

The gel had a pH of 4.1.

EXAMPLE 6

| Component | Amount grams |
| --- | --- |
| Flurbiprofen | 1.0 |
| Isopropyl Alcohol | 30.0 |
| Propylene Glycol | 15.0 |
| Polyethylene Glycol 400 | 5.0 |
| Carbomer 980 NF | 2.0 |
| Diisopropanolamine | <0.1 |
| Purified Water | q.s.a.d. |

The composition had a pH of 4.5.

EXAMPLE 7

| Component | Amount grams |
| --- | --- |
| Flurbiprofen | 1.00 |
| Isopropyl Alcohol | 30.0 |
| Propylene Glycol | 5.0 |
| Polyethylene Glycol 400 | 5.0 |
| Carbomer 980 NF | 2.0 |
| Diisopropanolamine | <0.1 |
| Purified Water | q.s.a.d. |

The gel had a pH of 4.3.

EXAMPLE 8

| Component | Amount grams |
| --- | --- |
| Flurbiprofen | 4.0 |
| Isopropyl Alcohol | 30.0 |
| Propylene Glycol | 5.0 |
| Polyethylene Glycol 400 | 5.0 |
| Carbomer 980 NF | 2.0 |
| Diisopropanolamine | 0.05 |
| Purified Water | 53.95 |

The gel had a pH of 4.1.

EXAMPLE 9

| Component | Amount grams |
| --- | --- |
| Flurbiprofen | 4.0 |
| Isopropyl Alcohol | 30.0 |
| Propylene Glycol | 5.0 |
| Polyethylene Glycol 400 | 5.0 |
| Cineole | 3.0 |
| Carbomer 980 NF | 2.0 |
| Diisopropanolamine | 0.05 |
| Purified Water | 50.95 |

The gel had a pH of 4.1.

EXAMPLE 10

| Component | Amount grams |
| --- | --- |
| Flurbiprofen | 4.0 |
| Isopropyl Alcohol | 30.0 |
| Propylene Glycol | 5.0 |
| Polyethylene Glycol 400 | 5.0 |
| Menthone | 3.0 |
| Carbomer 980 NF | 2.0 |
| Diisopropanolamine | 0.05 |
| Purified Water | 50.95 |

The gel had a pH of 4.1.

EXAMPLE 11

| Component | Amount grams |
| --- | --- |
| Flurbiprofen | 4.0 |
| Isopropyl Alcohol | 30.0 |
| Propylene Glycol | 5.0 |
| Polyethylene Glycol 400 | 5.0 |
| d-Limonene | 0.5 |
| Carbomer 980 NF | 2.0 |
| Diisopropanolamine | 0.05 |
| Purified Water | 53.45 |

The gel had a pH of 3.9.

EXAMPLE 12

| Component | Amount grams |
| --- | --- |
| Flurbiprofen | 4.0 |
| Isopropyl Alcohol | 30.0 |
| Propylene Glycol | 5.0 |
| Polyethylene Glycol 400 | 5.0 |
| Terpinen-4-ol | 0.5 |
| Carbomer 980 NF | 2.0 |
| Diisopropanolamine | 0.05 |
| Purified Water | 53.45 |

The gel had a pH of 4.3.

EXAMPLE 13

| Component | Amount grams |
| --- | --- |
| Flurbiprofen | 4.0 |
| Isopropyl Alcohol | 30.0 |
| Propylene Glycol | 5.0 |
| Polyethylene Glycol 400 | 5.0 |
| d-Limonene | 1.5 |
| Terpinen-4-ol | 1.5 |
| Carbomer 980 NF | 2.0 |
| Diisopropanolamine | 0.05 |
| Purified Water | 50.95 |

The gel had a pH of 4.3.

TEST PROCEDURE USED

Various hydroalcoholic flurbiprofen formulations, as described in the above examples, were tested for their relative effect in delivering flurbiprofen through human cadaver skin, as follows.

The total flux of flurbiprofen was measured over time using an automated system with 15 mm diameter 12.5 mL volume modified Franz diffusion cells. The receptor compartment of the cells contained isotonic phosphate buffer at pH 7.4+/−0.1 with the temperature controlled at 32° C. Human cadaver skin, previously dermatomed, was thawed and mounted onto the cells and left to hydrate for about one half hour prior to dosing. About 3.5 g of the formulation was placed onto the skin surface and was occluded with an impermeable covering. The automated system sampled and replaced about 0.8 mL from the receptor compartments at regular intervals. The samples were assayed for total flurbiprofen by high pressure liquid chromatography. The total amount of flurbiprofen transported through the skin was plotted versus time.

TEST RESULTS

Flurbiprofen gels having a pH of 2.2, 3.9, 5.0, and 6.5, as described in Examples 1, 2, 3, and 4, were tested according to the above test procedure. The tests measured the total amount of flurbiprofen (in micrograms) which diffused through human skin at various time intervals (in hours). The results are plotted on the graph in FIG. 3.

The diffusion data generated from the gels of Examples 1 (pH 6.5) and 2 (pH 3.9) was used to estimate the permeability coefficients of the ionized and non-ionized species. These coefficients were then used in Fick's Second Law to create the theoretical flux vs. pH profile show in FIG. 1.

Using the permeability coefficients discussed above, Fick's Second Law was used to calculate the theoretical, total flux of flurbiprofen at pH 5.0. This flux is reported as the simulated data in FIG. 2. The actual flurbiprofen diffused through human skin from the gel of Example 3 (pH 5.0) is plotted in FIG. 2 as the experimental data. The strong correlation between the simulated and the experimental data in FIG. 2 indicates that the model of FIG. 1 is predictive of flurbiprofen flux between pH 3.9 and 6.5.

Figure 3:
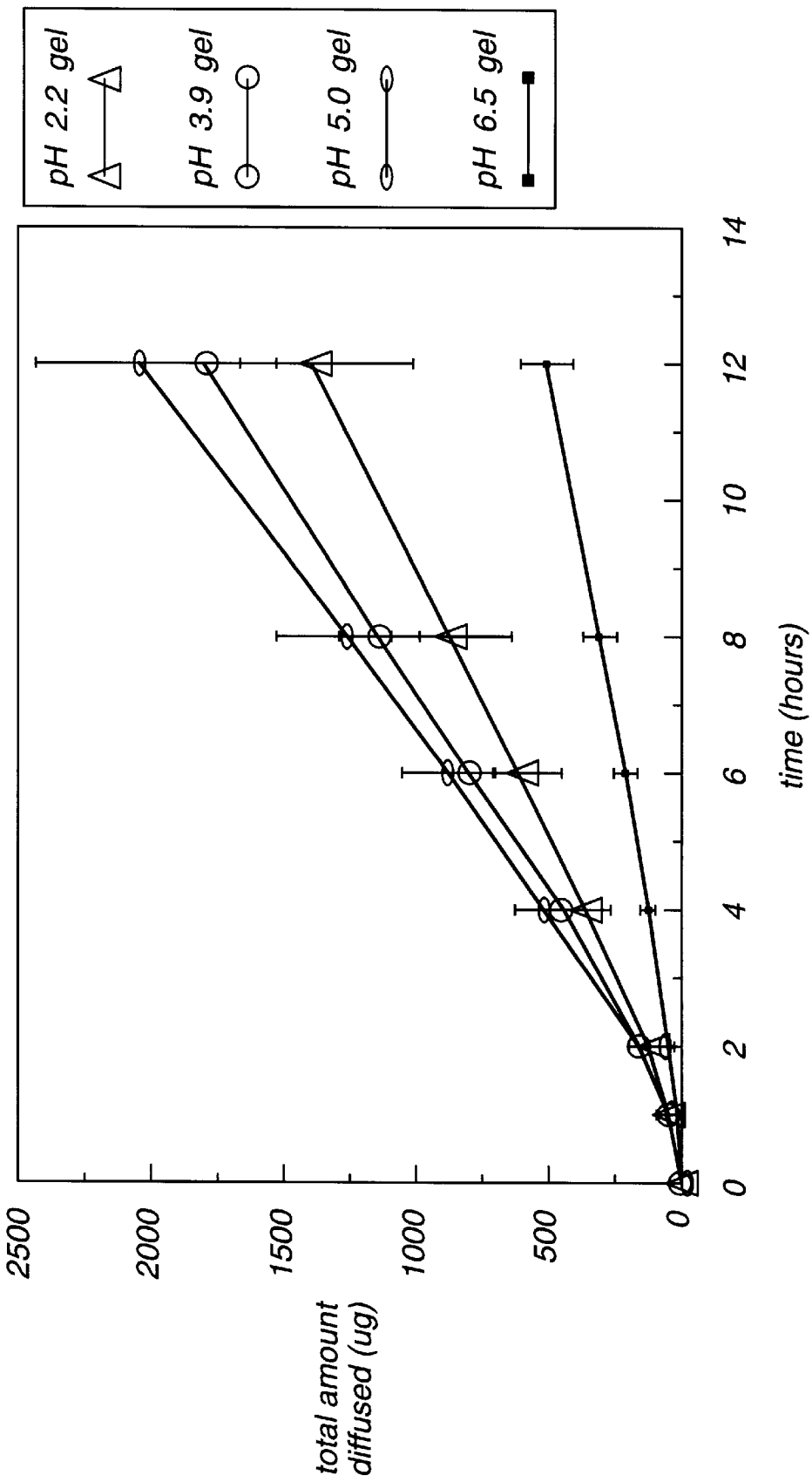
FIG. 3 is a graph plotting the effect of pH on the amount of flurbiprofen diffused through human cadaver skin between 0 and 12 hours.

FIG. 3 is a graph comparing the total amount of flurbiprofen diffused through human skin between zero and twelve hours whereby the pH 2.2 gel is described in Example 4 above, the pH 3.9 gel is described in Example 2, the pH 5.0 gel is described in Example 3, and the pH 6.5 gel is described in Example 1. High variability, as seen in the data in the graph, is common in data generated using human skin tissue. However, as can be seen from the graph, the data generated support the inventors' discovery that flurbiprofen-containing gels having a pH of 5 or lower are more effective at maximizing flurbiprofen diffusion through skin over time than a gel having a more neutral or basic pH, such as the gel of Example 1 which has a pH of 6.5.

Figure 2:
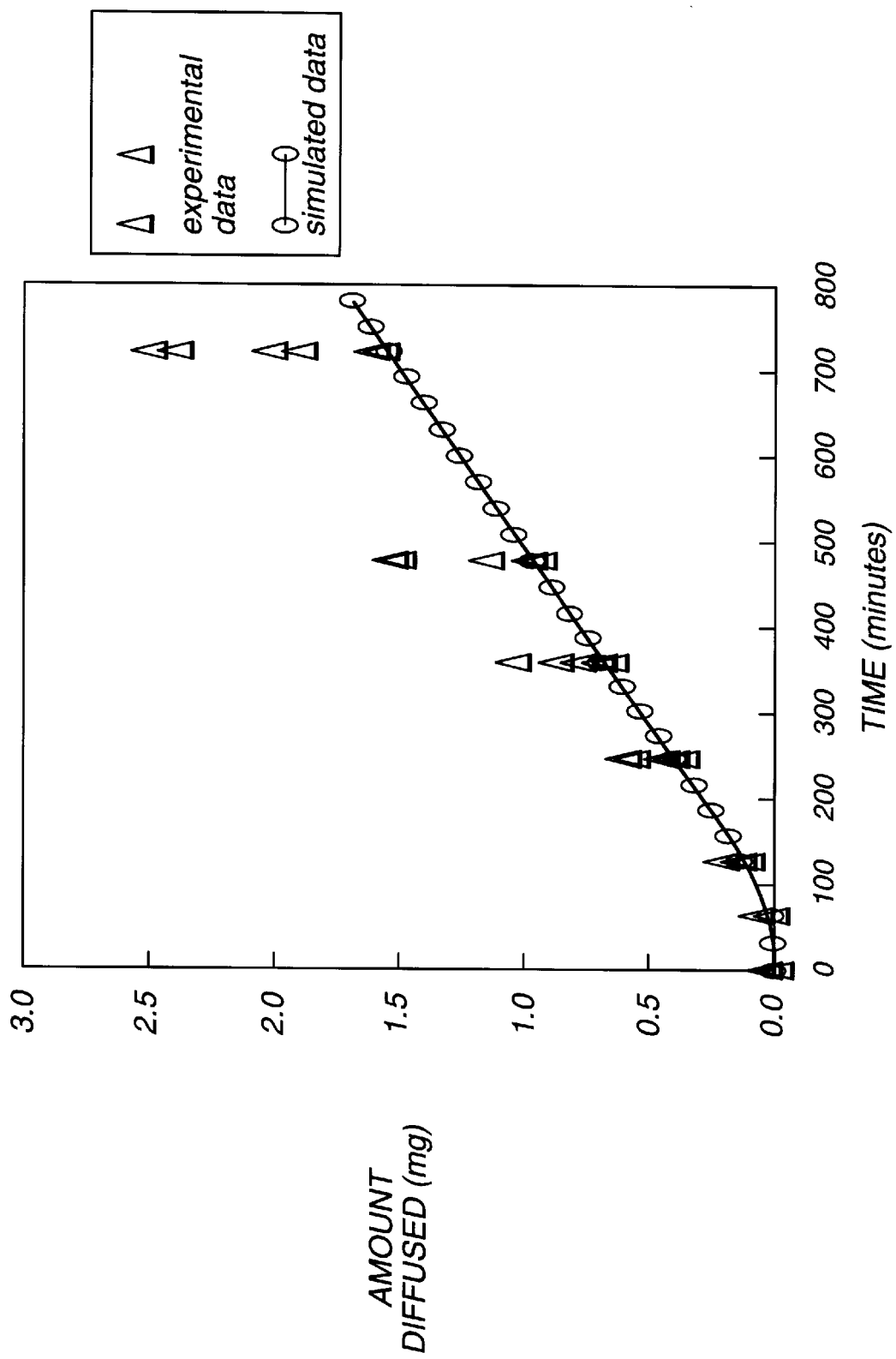
FIG. 2 is a graph comparing experimental data obtained from experiments completed on cadaver skin versus simulated data as determined from Fick's Second Law for the total amount of flurbiprofen diffused over time by a gel composition containing 2% flurbiprofen, 54% ethanol, and having a pKa of 5.7.

With respect to the gels having a pH of 2.2, 3.9 and 5.0, no further conclusions could be determined from FIG. 3 because the results were determined not to be statistically different due to the high variance in the data obtained. However, as shown in FIGS. 1 and 2, it is believed that flurbiprofen-containing gels having a pH of less than 4.5 are preferred in order to maximize drug delivery and, more importantly, to maintain such optimal flux or drug delivery rates throughout the shelf life of the product.

The scope of the present invention is not limited by the description, examples and suggested uses herein and modifications can be made without departing from the spirit of the invention. For example, additional medicaments or counter-irritants may be added to the hydroalcoholic gel to provide a combination medication.

Application of the compositions and methods of the present invention for medical and pharmaceutical uses can be accomplished by any clinical, medical and pharmaceutical methods and techniques as are presently or prospectively known to those skilled in the art. Thus it is intended that the present invention cover the modifications and variations of this invention provided that they come within the scope of the appended claims and their equivalents.

What is claimed is:

1. A pharmaceutical composition for topical application comprising, by weight of the total weight of the composition:
   (a) about 0.5 to 10% flurbiprofen;
   (b) about 10 to 80% of a lower alcohol;
   (c) about 0 to 25% of a glycol;
   (d) about 0 to 5% of a gelling agent;
   (e) an amount of a pH adjusting agent sufficient to adjust the pH of the composition to a range of from about 2 to less than 4.5; and
   (f) water in an amount sufficient to make up the balance of the composition.

2. The composition of claim 1 containing an amount of a pH adjusting agent sufficient to adjust the pH to a range of from about 3.5 to 4.

3. The composition of claim 1 containing an amount of a pH adjusting agent sufficient to adjust the pH to a range of about 4.

4. The composition of claim 1 wherein the amount of pH adjusting agent is less than about 0.05%.

5. The composition of claim 1 wherein the lower alcohol is selected from the group consisting of ethanol, propanol, and isopropanol.

6. The composition of claim 1 wherein the glycol is selected from the group consisting of butylene glycol, propylene glycol, polypropylene glycol, polyethylene glycol, polyethylene glycol dodecyl ether, and glycerine.

7. The composition of claim 1 wherein the gelling agent is selected from the group consisting of carboxyvinyl polymers, hydroxycellulose, hydroxyethyl cellulose, hydroxypropylmethyl cellulose, methylcellulose, carboxymethylcellulose, hydroxypropyl cellulose, and alginic acid-propylene glycol ester.

8. The composition of claim 1 wherein said pH adjusting agent is selected from the group consisting of sodium hydroxide, potassium hydroxide, diisopropanolamine, triethanolamine, and triethylamine.

9. The composition of claim 1 further comprising up to about 10% of a penetration enhancer.

10. The compositon of claim 9 wherein the penetration enhancer is selected from the group consisting of terpenes, terpene alcohols and essential oils.

11. The composition of claim 10 wherein the penetration enhancer is selected from the group consisting of d-limonene, terpinen-4-ol, menthone, 1,8-cineole, 1-pinene, a-terpineol, carveol, carvone, pulegone, piperitone, ascaridole, ylang, anise, chenopodium, eucalyptus, 3-carene, cyclohexene oxide, limonene oxide, a-pinene oxide, cyclopentene oxide, and 7-oxabicyclo[2.2.1]-heptane, eucalyptol, and peppermint oil.

12. The composition of claim 1 which is a gel, a spray, an aerosol, a lotion, a cream, or an ointment.

13. The composition of claim 1 which is a gel.

14. The composition of claim 1 having a viscosity of from about 50,00 to 1.5 million centipoises at ambient temperature.

15. The composition of claim 1, comprising:
   (a) about 1 to 5% flurbiprofen;
   (b) about 30 to 55% of a lower alcohol;
   (c) about 5 to 15% of a glycol;
   (d) about 0.5 to 2% of a gelling agent;
   (e) an amount of a pH adjusting agent sufficient to adjust the pH to a range of from about 2.5 to less than 4.5; and
   (f) water q.s. to 100%.

16. The composition of claim 15 containing an amount of a pH adjusting agent sufficient to adjust the pH to a range of from about 3.5 to 4.

17. The composition of claim 15 containing an amount of a pH adjusting agent sufficient to adjust the pH to a range of about 4.

18. The composition of claim 15 wherein the amount of pH adjusting agent is less than about 0.05%.

19. The composition of claim 1 comprising:
   (g) about 4% flurbiprofen;
   (h) about 30% of a lower alcohol selected from the group consisting of ethanol, propanol and isopropanol;
   (i) about 10% of a glycol selected from the group consisting of propylene glycol, butylene glycol, polyethylene glycol, polypropylene glycol, polyethylene glycol dodecyl ether and glycerine;
   (j) about 2% of a gelling agent selected from the group consisting of carboxyvinyl polymers, hydroxycellulose, methylcellulose, hydroxyethyl cellulose, carboxymethylcellulose, hydroxypropyl cellulose, and hydroxyproplymethyl cellulose;
   (k) about 0.05% of a pH adjusting agent, said amount being sufficient to adjust the pH to a range of about 4 and said pH adjusting agent being selected from the group consisting of diisopropanolamine, triethanolamine, and triethylamine;
   (l) water q.s. to 100%; and
   (m) optionally, a penetration enhancer.

20. A method for delivering flurbiprofen through the skin comprising the step of topically administering the flurbiprofen-containing-composition of claim 1 to the skin of the patient.

21. A method for delivering flurbiprofen through the skin comprising the step of topically administering the flurbiprofen-containing-composition of claim 12 to the skin of the patient.

22. A method for delivering flurbiprofen through the skin comprising the step of topically administering the flurbiprofen-containing-composition of claim 16 to the skin of the patient.

* * * * *